United States Patent
Sprenger-Haussels (10) Patent No.: US 9,890,413 B2
(45) Date of Patent: *Feb. 13, 2018

(54) ISOLATION OF NUCLEIC ACID FROM STOOL SAMPLES AND OTHER BIOLOGICAL MATERIALS WHICH ARE RICH IN INHIBITORS

(75) Inventor: Markus Sprenger-Haussels, Solingen (DE)

(73) Assignee: QIAGEN GMBH, Hilden (DE)

( * ) Notice: Subject to any disclaimer, the term of this patent is extended or adjusted under 35 U.S.C. 154(b) by 978 days.

This patent is subject to a terminal disclaimer.

(21) Appl. No.: 11/338,002

(22) Filed: Jan. 24, 2006

(65) Prior Publication Data

US 2006/0172331 A1  Aug. 3, 2006

Related U.S. Application Data

(62) Division of application No. 10/182,950, filed as application No. PCT/EP01/00515 on Jan. 18, 2001, now Pat. No. 7,005,266.

(30) Foreign Application Priority Data

Feb. 4, 2000 (DE) .................................. 100 04 927
Mar. 17, 2000 (DE) .................................. 100 13 225

(51) Int. Cl.
C12Q 1/68  (2006.01)
(52) U.S. Cl.
CPC .................................. C12Q 1/6806 (2013.01)
(58) Field of Classification Search
None
See application file for complete search history.

(56) References Cited

U.S. PATENT DOCUMENTS

| | | | |
|---|---|---|---|
| 4,935,342 A | | 6/1990 | Seligson et al. |
| 5,808,041 A | * | 9/1998 | Padhye et al. ............... 536/25.4 |
| 5,866,787 A | * | 2/1999 | Silverman et al. .......... 800/301 |
| 6,037,465 A | * | 3/2000 | Hillebrand et al. ....... 536/25.42 |
| 6,084,091 A | | 7/2000 | Müller et al. |
| 6,274,386 B1 | * | 8/2001 | Harttig .......................... 436/526 |
| 6,383,393 B1 | * | 5/2002 | Colpan et al. ................ 210/656 |
| 6,383,783 B1 | * | 5/2002 | Haddad ........................ 435/91.1 |
| 6,992,182 B1 | * | 1/2006 | Muller et al. ............... 536/25.41 |
| 7,005,266 B2 | * | 2/2006 | Sprenger-Haussels ........... 435/6 |

FOREIGN PATENT DOCUMENTS

| | | | |
|---|---|---|---|
| EP | | 811694 A2 | * 12/1997 |
| WO | | WO 93/20235 | 10/1993 |
| WO | | WO 95/01359 | 1/1995 |
| WO | | WO 9534569 A1 | * 12/1995 |
| WO | | WO 97/07239 | 2/1997 |

OTHER PUBLICATIONS

Too et al. Simultaneous extraction of total RNA and peptides from tissues: Application to tachykinins. Peptides (1995) 16(1): 45-53.*
Pich et al. Midiprep method for isolation of DNA from plants with a high content of polyphenolics. Nucleic Acids Research (1993) 21(14): 3328.*
Kong et al. DNA extraction conditions from Porphyra perforate using LiCl. Journal of Applied Phycology 7:101-107 (1995).*
Norris et al. The vitamin B and vitamin C content of marine algae. The Journal of Nutrition (1936) 13(4): 425-433.*
Kuntzman, G. Tobacco in your tiramasu? Newsweek (2003) 5 printed pages.*
Lawson et al. Journal of Applied Microbiology (1997) 83: 375-380.*
Robinson et al. Langmuir 2002; 18: 8743-8748. (Year: 2002).*
Stuart et al. Journal of Colloid and Interface Science 1982; 90: 310-320. (Year: 1982).*
Chung et al., *Chem. Abstr.*, 127: 146699x (1997).
de Kok et al., *Clin. Chem.*, 44(10): 2201-2204 (1998).
Deuter et al., *Nucleic Acids Res.*, 23(18): 3800-3801 (1995).
Hopwood et al., *Int. J. Legal Med.*, 108: 237-243 (1996).
Monteiro et al., *J. Clin. Microbiol.*, 35(4): 995-998 (1997).
Pantosti et al., *J. Clin. Microbiol.*, 35(10): 2482-2486 (1997).
Ramamurthy et al., *J. Clin. Microbiol.*, 31(11): 3068-3070 (1993).
Sidransky et al., *Science*, 256: 102-105 (1992).
Sivolap et al., *Chem. Abstr.*, 117: 206001u (1992).
Tuchili et al., *J. Vet. Med. Sci.*, 58(9): 881-884 (1996).
Uwatoko et al., *Vet. Microbiol.*, 52: 73-79 (1996).
Wan et al., Analytical Biochemistry, 223: 7-12 (1994).
van Zwet et al., *J. Clin. Microbiol.*, 32(5): 1346-1348 (1994).
Wang et al., *Anal. Biochem.*, 269: 198-201 (1999).
Wilde et al., *J. Clin. Microbiol.*, 28(6): 1300-1307 (1990).

* cited by examiner

*Primary Examiner* — Angela M Bertagna
(74) *Attorney, Agent, or Firm* — Medler Ferro Woodhouse & Mills PLLC (57) ABSTRACT

The invention related to a method for the stabilization, purification or/and isolation of nucleic acids from material samples, in particular, stool samples, which can contain impurities and inhibitors or interfering substances. The invention further relates to a reagent kit for carrying out this method. The basis of the invention is, in particular, a method for purification, stabilization or/and isolation of nucleic acids from material samples, whereby a buffer is added to the sample containing the nucleic acids, with a pH value of 2 to 7, a salt concentration of at least 100 mM, or/and a phenol neutralizing substance. According to the invention, pure nucleic acids which may be amplified can be obtained from faecal samples by a simple method, which are suitable for diagnostic proof of infection, in particular, bacterial or viral infection, or mutation, in particular, for tumor-specific DNA mutations.

28 Claims, 12 Drawing Sheets

ISOLATION OF NUCLEIC ACID FROM STOOL SAMPLES AND OTHER BIOLOGICAL MATERIALS WHICH ARE RICH IN INHIBITORS

CROSS-REFERENCE TO RELATED APPLICATIONS

The present application is a division of U.S. application Ser. No. 10/182,950, filed Aug. 2, 2002, now U.S. Pat. No. 7,005,266 issued Feb. 28, 2006, which is the US national phase of international application PCT/EP01/00515, filed Jan. 18, 2001 and designating the United States, which international application claims priority to DE 100 04 927.3, filed Feb. 4, 2000 and DE 100 13 225.1, filed Mar. 17, 2000.

The invention relates to a process for stabilising, purifying and/or isolating nucleic acids from samples of material, particularly stool samples, which may contain impurities and inhibitors or unwanted substances. A reagent kit suitable for carrying out the process is also described.

Numerous examples from various fields of research have confirmed the importance of analysing nucleic acids from biological materials contaminated with substances which damage nucleic acids during storage and inhibit enzymatic manipulation of the nucleic acids, e.g. digestion with restriction enzymes or amplification by polymerase chain reaction (PCR). Therefore, in order to be able to use the nucleic acids contained in the biological materials for further analysis, it is important that these substances should be present only in very low concentrations or should be eliminated entirely from the sample.

Analysis of nucleic acids from faecal samples is particularly important. One major medical application is the detection of tumour-specific changes in human nuclear DNA from stools, which may be used as a parameter in the early diagnosis of tumours of the digestive tract. Similarly, the detection of bacterial and viral infectious agents from stool samples by means of test processes based on nucleic acids is becoming increasingly important.

For purifying nucleic acids from stool samples it is common to use a combination of different purification steps such as protease treatment, phenol/chloroform extraction, binding of nucleic acids to silica in the presence of chaotropic salts, gel filtration, anion exchange chromatography and the use of cationic detergents. The nucleic acids isolated from stool samples by these methods are, however, generally unstable and often behave problematically in subsequent enzymatic reactions such as PCR, for example. The reasons for this are substances which are isolated together with the nucleic acid which damage it and inhibit enzymatic reactions. Types of inhibitor contained in the stools include—so far as is known—haemoglobin and the metabolites thereof, bile acids and bile acid derivatives as well as polysaccharides. There are various proposed solutions to this problem in the prior art but none of them give satisfactory results (Deuter et al., Nucleic Acids Res. 1995, 23: 3800-3801; van Zwet et al., J. Clin. Microbiol, 1994, 32: 1346-1348; Wilde et al, J. Clin Microbiol. 1990, 28: 1300-1307; Hopwood et al., Int. J. Legal Med. 1996, 108: 237-243; Sidransky et al., Science 1992, 256: 103-105; Ramamurthy et al., J. Clin. Microbiol. 1993, 31: 3068-3070; Monteiro et al., J. Clin. Microbiol. 1997, 35: 995-998; Uwatoko et al., Vet. Microbiol. 1996, 52: 73-79; Tuchili et al., J. Vet. Med. Sci. 1996, 58: 881-884; Pantosti et al., J. Clin. Microbiol. 1997, 35: 2482-2486, U.S. Pat. No. 4,935,342; WO 93/20235). As a rule the sample is worked up in an alkaline medium.

Sivolap et al., Chem. Abstr. 1992, 117:206001u describe the addition of phenol-neutralising substances when isolating DNA from plant material. Chung et al., Chem. Abstr. 1997, 127:146699x describe the extraction of DNA from plant material using a basic buffer.

WO 97/07239 describes a method of purifying, stabilising and/or isolating nucleic acids from biological materials, particularly faecal material, in which an adsorption matrix is added to a sample of biological materials containing nucleic acids in order to bind any impurities. Preferably, an adsorption matrix based on carbohydrate is used, e.g. one based on starch, cellulose, glycogen and/or other biogenic or non-biogenic carbohydrates or mixtures thereof, while flours made from wheat, peas, maize, potatoes or ingredients thereof or their mixtures are preferred. However, in many cases, the substances which damage nucleic acids are not totally eliminated using the method disclosed in WO 97/07239.

A further development of this process is disclosed in DE 199 00 638.5. This describes a process for isolating nucleic acids from biological materials in which as well as the adsorption matrix for binding impurities a specific buffer is added to the sample containing the nucleic acids, the buffer being characterised in that it has an acid to neutral pH and a high salt content and contains a phenol-neutralising substance. This process does indeed yield nucleic acids with sufficiently high purity but has the disadvantage that the adsorption matrix described swells considerably and makes homogenisation more difficult. This is particularly the case after the action of heat, which is beneficial for lysing bacteria, viruses and other pathogens.

One aim of the present invention was thus to provide an improved process for purifying nucleic acids which overcomes the disadvantages of the methods known from the prior art described above.

It was found, surprisingly, that the purification of nucleic acids from inhibitory samples can be improved by using a specific buffer without having to add an adsorption matrix as described in WO 97/07239 or DE 199 00 628.5 to the sample in order to bind impurities.

The present invention relates to a process for purifying, stabilising and/or isolating nucleic acids from samples of material, in which a buffer is added to the sample containing the nucleic acids, this buffer
(a) having a pH of 2 to 7, preferably less than 7,
(b) having a salt concentration of at least 100 mmol/l, and/or
(c) containing a phenol-neutralising substance,
the process being characterised in that no adsorption matrix based on carbohydrates is added to the sample, the mixture of sample and buffer or a homogenised or lysed material or extract derived therefrom.

Adsorption matrices of this kind for binding impurities are described in the patent applications WO 97/07239 and DE 199 00 628.5, the entire contents of these are hereby referred.

The buffer preferably has a salt concentration of 100 mmol/l up to the solubility limit of the salt used. Preferred ranges are 100 mmol/l to 2.5 mol/l, more preferably 250 to 2.5 mol/l, particularly 300 mmol/l to 1.5 mol/l, most preferably 300 mmol/l to 700 mmol/l. A particularly preferred range is 400 mmol/l to 600 mmol/l. By the word salt is meant here inorganic salts, particularly alkali or alkaline earth metal salts of inorganic acids. Preferably, an alkali metal halide, e.g. NaCl or KCl or mixtures thereof are used as the salt.

In another preferred embodiment LiCl is used as the salt. The concentration used may range from 100 mmol/l up to the limit of solubility. If LiCl is used a concentration of 0.5 mol/l up to the limit of solubility, most preferably from 0.5 to 2.5 mol/l is preferred.

In another embodiment the buffer according to the invention contains at least 0.1% (wt./vol) of a detergent, preferably at least 0.5%. The detergent used is preferably an ionic detergent, especially sodium dodecylsulfate (SDS) in a concentration of from 0.1 to 5% (wt./vol) more preferably 0.5 to 5% (wt./vol), most preferably 1 to 2% (wt./vol).

In another embodiment the buffer according to the invention may contain 1 to 200 mmol/l, preferably 10 mmol/l or more than 10 mmol/l, most preferably at least 20 mmol/l of a chelating agent. A particularly preferably range is 25 to 75 mmol/l. Ethylenediamine-tetraacetic acid (EDTA) or a salt thereof, especially the disodium salt, is preferred.

The buffer according to the invention preferably has a pH of more than 3 but less than 7, preferably from 4 to 6.5, more preferably from 4 to 6. It has proved advantageous to use acetate buffers, e.g. acetic acid/Na-acetate (NaAc). However, other buffers such as phosphate or citric buffers may also be used.

The buffer according to the invention preferably contains at least one phenol-neutralising substance. Preferred examples of substances which can neutralise phenols are polyvinylpyrrolidone (poly(1-vinyl-2-pyrrolidone), PVP, CAS 9003-39-8; obtainable for example from Sigma-Aldrich Fine Chemicals, St. Louis, Mo., USA) in various polymerisation levels, e.g. PVP-10 (PVP with an average molecular weight of 10,000), reducing agents, e.g. thiol reagents such as β-mercaptoethanol or dithiothreitol, or borates. A buffer which contains at least 0.5% polyvinylpyrrolidone as phenol-neutralising substance is preferred. Preferred ranges of concentration are from 1-30% (wt./vol) preferably 2-15%, most preferably 4-10% PVP.

The buffer according to the invention is preferably a lysing buffer, i.e. it preferably has a composition which brings about the lysing of cells, particularly the lysing of cells which contain the nucleic acids which are of interest in the present instance. The skilled man will be familiar with the conditions (e.g. concentrations of ions and/or detergent) under which the lysing (i.e. perforation, destruction or dissolving of the cell membranes and/or cell walls) of the desired cells such as microorganisms, animal or plant cells takes place.

The sample containing nucleic acids is preferably obtained from materials which contain impurities that break down nucleic acids or inhibit enzymatic reactions. In particular, impurities of this kind inhibit the enzymatic activity of restriction enzymes and enzymes which are used for polymerase chain reaction (PCR). Preferably, the sample consists of faecal material. However, it may also be obtained from other sources, e.g. animal or plant tissues, tissue or cell cultures, bone marrow, human and animal body fluids such as blood, serum, plasma, urine, sperm, cerebrospinal fluid, sputum and smears, plants, parts of plants and plant extracts, e.g. saps, fungi, prokaryotic or eukaryotic microorganisms such as bacteria or yeasts, fossilised or mummified samples, soil samples, clarified sludge, sewage and foodstuffs (particularly processed i.e. industrially prepared foodstuffs). The samples may contain water-insoluble ingredients.

In another aspect the invention relates to a process as hereinbefore described in which the mixture of sample and buffer or a homogenised or lysed material or extract derive therefrom is incubated at at least 50° C.

In another aspect the invention relates to the use of a process as hereinbefore described for analysing, detecting or isolating nucleic acids from stool samples.

In another aspect the invention relates to a reagent kit for purifying, stabilising and/or isolating nucleic acids from biological materials, containing a buffer as hereinbefore described, particularly a buffer which
 (a) has a pH of 2 to 7, preferably less than 7,
 (b) has a salt concentration of at least 100 mmol/l, and/or contains a phenol-neutralising substance.

The reagent kit according to the invention is characterised in that it does not contain a carbohydrate-based adsorption matrix as described in patent applications WO 97/07239 and DE 199 00 628.5.

The buffer may be present in finished form, as a concentrate or lyophilisate.

Preferably, the reagent kit contains additional means for purifying nucleic acids which comprise, for example, inorganic and/or organic carriers and optionally solutions, excipients and/or accessories. Such agents are known from the prior art (c.f. for example WO 95/01359) and are commercially available. Inorganic components of carriers may be, for example, porous or non-porous metal oxides or mixed metal oxides, e.g. aluminium oxide, titanium dioxide, iron oxide or zirconium dioxide, silica gels, materials based on glass, e.g. modified or unmodified glass particles or ground glass, quartz, zeolite or mixtures of one or more of the above-mentioned substances. On the other hand, the carrier may also contain organic ingredients which may be selected, for example, from latex particles optionally modified with functional groups, synthetic polymers such as polyethylene, polypropylene, polyvinylidene fluoride, particularly ultra high molecular polyethylene or HD-polyethylene, or mixtures of one or more of the above-mentioned substances.

The carrier may be used, for example, in the form of particles with an average size of 0.1 µm to 100 µm. When a porous carrier is used an average pore size of 2 µm to 100 µm is preferred. The carrier may for example be in the form of loose particles, filter layers, e.g. of glass, quartz or ceramic, membranes, e.g. membranes containing a silica gel, fibres or fabrics woven from inorganic carriers such as quartz or glass wool and in the form of lattices or sintered materials from synthetic polymers.

In addition, the reagent kit according to the invention may also contain excipients such as, for example, a protease such as proteinase K, or enzymes and other agents for manipulating nucleic acids, e.g. at least one amplification primer, and enzymes suitable for amplifying nucleic acids, e.g. a nucleic acid polymerase and/or at least one restriction endonuclease.

The primers for amplifying nucleic acids are preferably obtained from the genes which are to be analysed, i.e. from oncogenes, tumour suppressor genes and/or micro-satellite, for example, or they may be suitable for amplifying viral or bacterial nucleic acid sequences. Enzymes and restriction endonucleases suitable for amplifying nucleic acids are known and commercially available.

In another aspect the invention relates to a process for purifying, stabilising and/or isolating nucleic acids from samples of material comprising the following steps:
 (a) taking a sample of material containing nucleic acids,
 (b) adding a buffer which has a pH of 2 to 7, preferably less than 7, a salt concentration of at least 100 mmol/l, and/or contains a phenol-neutralising substance, characterised in that no adsorption matrix based on carbohydrates is added to the sample, the mixture of sample and buffer or an extract, lysate or homogenisate derived therefrom.

Preferably the sample is a sample of material which contains impurities that break down nucleic acid or inhibit enzymatic reactions. In particular, such impurities inhibit the enzymatic activity of enzymes that interact with nucleic acid, e.g. nucleases such as restriction endonucleases, reverse transcriptases, nucleic acid polymerases, ligases, etc., particularly enzymes which are used for polymerase chain reaction (PCR), LCR (ligase chain reaction), NASBA (nucleic acid base specific amplification) or 3SR (self sustained sequence replication). Preferred embodiments of the buffer are as hereinbefore described.

In another aspect the invention relates to a process of this kind comprising the following steps:
(a) taking a sample of material containing nucleic acids,
(b) adding a buffer which has a pH of 2 to 7, preferably less than 7, a salt concentration of at least 100 mmol/l, and/or containing a phenol neutralising substance, and
(c) homogenising the mixture of sample and buffer.

In another the aspect the invention relates to a process of this kind comprising the steps of:
(a) taking a sample of material containing nucleic acids,
(b) homogenising the material and
(c) adding a buffer which has a pH of 2 to 7, preferably less than 7 and a salt concentration of at least 100 mmol/l, and/or containing a phenol-neutralising substance.

By homogenisation is meant a mechanical, thermal, enzymatic or chemical breaking down of material samples or sample ingredients, particularly water-insoluble samples of material. Homogenisation may be achieved using methods known per se, e.g. using a conventional vibrating mixer for microcentrifugation vessels (vortex shaker), an Ultratarax or Polytran, a French Press, a potter, a mortar or a ball mill.

In further steps, insoluble ingredients may be separated off by centrifugation, a protease may be added to the extract and/or the extract may be heated to ≥50° C.

The steps described (addition of the buffer according to the invention, homogenisation, centrifugation, addition of a protease, heating), if they are carried out, may be carried out in a different order if necessary. Thus, the buffer according to the invention may first be added to the sample which is optionally coarsely ground, after which homogenisation followed by centrifugation may be carried out. If the buffer has lytic properties, the centrifugation conditions used must be different from those used when the buffer is non-lysing and cell lysis is only achieved at a later stage, since in the latter case care must be taken to ensure that the cells which contain the desired nucleic acids are not lost during centrifugation. If, on the other hand, nucleic acids are to be isolated from viruses which are present in extra cellular form in the material sample, it may be desirable to use a non-lytic buffer and, after the buffer has been added and the homogenisation has been carried out, to separate the cells contained in the sample together with other insoluble ingredients by centrifugation.

The break-up of the material sample as described above may be followed by chromatographic purification or isolation of the nucleic acids in known manner, e.g. through a silica gel membrane in a centrifugation column in the presence of chaotropic salts.

One way of carrying out the invention is to mix a material sample with the buffer according to the invention and if necessary to homogenise the mixture. Homogenisation may be done, for example, using a vortex shaker. These steps may be carried out at ambient temperature or preferably at reduced temperature, e.g. ≤10° C., particularly ≤4° C. After any homogenisation has been completed, insoluble matter may be separated off. If the cells have already been lysed at this stage, e.g. because the buffer according to the invention has lytic properties, the insoluble ingredients may be separated off for example by centrifugation for 1 to 5 minutes at 10,000 to 25,000×g, preferably at 20,000×g.

It may be necessary to incubate the resulting extract or the resulting lysate under conditions which are necessary for releasing the nucleic acids from the sample material. Incubation conditions of this kind are used particularly when nucleic acids are to be detected in materials which are "difficult" to open up, e.g. bacteria or parasites or viruses. In this case, the release of the nucleic acids may be improved by chemical, thermal and/or enzymatic treatment, resulting in a higher yield of nucleic acids from the sample material both in terms of total DNA and specifically with regard to the DNA which is to be detected. Preferably, the temperature is increased, e.g. to ≥50° C., particularly to ≥70° C.

If on the other hand nucleic acids from easily openable material such as sensitive cells such as human cells, for example, are to be determined, it may be advantageous to carry out the process of extraction and cell opening at reduced temperature, e.g. ≤10° C., particularly ≤4° C. in order to avoid or restrict the unwanted release of other nucleic acids in the sample in this way.

Treatment with the buffer according to the invention results in very good stability of the nucleic acids contained in the sample and when the nucleic acids are subsequently isolated it leads to better reproducibility without the need to carry out the additional steps of addition, incubation and subsequent removal of an adsorption matrix in order to bind impurities. This is particularly true if the isolation is followed by an enzymatic manipulation of the nucleic acids with enzymes that interact with nucleic acid, e.g. nucleases such as restriction endonucleases, reverse transcriptases, nucleic acid polymerases, ligases, etc. Most preferably, the process according to the invention is followed by amplification and/or restriction cleaving, e.g. amplification by PCR, LCR (ligase chain reaction), NASBA (nucleic acid base specific amplification) or 3SR (self sustained sequence replication).

A particularly preferred aspect of the present invention is the analysis, detection or isolation of nucleic acids, particularly DNA, from stool samples. Using the process according to the invention, clean and amplifiable nucleic acids can easily be obtained from faecal samples and can then be used for the diagnostic detection of infections, particularly bacterial or viral infections, or mutations, particularly tumor specific DNA mutations.

The invention will be illustrated by the figures and examples that follow.

EXAMPLES

Example 1: Isolation of DNA from Stool Samples

Human stool samples were collected, frozen and stored at −20° C. 200 mg of stool were weighed in a 2 ml microcentrifuge container and cooled on ice. Then the stool sample was taken up in 1600 µl of buffer P1 (100 mmol/l NaAc pH 5.5, 50 mmol/l EDTA, 500 mmol/l NaCl, 2% (wt/vol) PVP-10, 1.4% (wt/vol) SDS) and the mixture was homogenised for 1 minute by treating in a vortex. The lysate was centrifuged for 3 minutes to precipitate stool particles and other impurities at 20,000×g (14,000 rpm in the Eppendorf 5417C centrifuge used; rotor FA 45-30-11). 1250 µl of the supernatant were transferred into a new 2 ml microcentrifuge container and mixed by inverting. 600 µl of this lysate were transferred into a new 2 ml microcentrifugation vessel and further purified with a commercially obtainable DNA purification kit (QIAamp® DNA Mini Kit, Qiagen GmbH, Hilden, Germany) in accordance with the manufacturers' instructions. These purification steps included the addition of proteinase-K, incubating for 10 minutes at 70° C. and purifying the nucleic acids by chromatography over a silica gel membrane in a centrifugation column in the presence of chaotropic salts. The DNA eluate thus obtained had a volume of 200 µl.

Example 2: Isolation of DNA from Stool Samples with and without the Use of a Carbohydrate Matrix Human stool samples were collected, frozen and stored at −20° C. DNA was isolated from a total of 16 different stool samples using various methods and then investigated quantitatively for inhibitors using a PCR method ("real time quantitative PCR"; SFV TaqMan® reaction; SFV=Semliki Forest Virus; Wang & Brown, Anal. Biochem. 1999, 269: 198-201; de Kok et al., Clin. Chem. 1998, 44:2201-2204).

V1-V3: 1600 mg of stool were placed in a 50 ml centrifuge tube and cooled on ice. Then the stool sample was taken up in 12.8 ml of buffer P1 (100 mmol/l NaAc pH 5.5, 50 mmol/l EDTA, 500 mmol/l NaCl, 2% (wt/vol) PVP-10, 1.4% (wt/vol) SDS) and the mixture was homogenised by vortex treatment for 1 minute. In order to pellet any insoluble ingredients in the stool, the mixture was centrifuged for 3 minutes at 5000 rpm (corresponding to 5338 g in the Sigma 4K15 centrifuge used, rotor 1156). The supernatant was transferred into a new 50 ml centrifuge tube and centrifuged again for 3 minutes at 5000 rpm. The supernatant was then transferred into another 50 ml centrifuge tube and mixed by inverting. The lysate thus obtained was divided into aliquots of 1400 µl in 20 ml microcentrifuge containers and used for the following three processes:

V1: 500 mg of a powdered absorption matrix consisting of potato flour and cellulose (mixed in the ratio 3:1 [wt/wt]) were added to the lysate and resuspended by vortex treatment for 1 minute.

V2: 500 mg of an adsorption matrix in tablet form consisting of potato flour and cellulose (mixed in the ratio 3:1 [wt/wt]; plus Mg-stearate as the tableting excipient) were added to the lysate and resuspended by vortex treatment for 1 min.

V3: No adsorption matrix was added to the lysate.

Further processing was identical in all three processes. The suspension (V1 and V2) and the untreated lysate (V3) were centrifuged for 3 minutes to precipitate any stool particles, the adsorption matrix and other impurities at 20,000×g (14,000 rpm in the centrifuge used, cf Example 1). The supernatant was transferred into a new microcentrifugation vessel and centrifuged for another 3 minutes. 600 µl of the supernatant from the second centrifugation were transferred into a new 2 ml microcentrifugation vessel and further purified with a commercially obtainable DNA purification kit (QIAamp® DNA Mini Kit, Qiagen GmbH, Hilden, Germany) in accordance with the manufacturers' instructions. These purification steps included the addition of proteinase K, incubation for 10 minutes 1 t 70° C. and chromatographic purification of the nucleic acids through a silica gel membrane in a centrifugation column in the presence of chaotropic salts. The DNA eluate obtained had a volume of 200 µl.

The DNA eluates from processes V1, V2 and V3 were qualitatively investigated for inhibitors using an SFV Taq-Man reaction (TaqMan®, Perkin Elmer Biosystems, Foster City, Calif., USA) (PCR over 50 cycles). For this purpose, 1000 copies of plasmid pSFV1 (Gibco BRL Life Technologies, Inc., Gaithersburg, Md., USA) were added, per batch, to a PCR mastermix. This plasmid containing sequences of Semliki Forest Virus foreign to the stool. The amplicon is located in the small nsP1 reading frame of the plasmid. The mastermix further contains 1× TaqMan Buffer A (Perkin Elmer), 3 mmol/l $MgCl_2$ (Perkin Elmer), 200 µM DATP, dCTP, dGTP, 400 µM dUTP (Perkin Elmer), 300 µM each of primer, 100 µM of sample, 1-10 ng/µl of BSA (New England Biolabs BSA007), 0.025 U/µl Amplitaq Gold (Perkin Elmer) and 0.01 U/µl of UNG (Perkin Elmer). In addition, the total volume of 25 µl contained 5 µl of DNA eluate from stool. If there were inhibitory substances present in the stool, the amplification of the SFV amplicon was delayed (increasing Ct values) and in extreme cases totally inhibited (Ct=50). As a positive control, instead of the DNA eluates, 5 µl of the eluting buffer P2 used in all the processes (10 mmol/l Tris-HCl pH 9.0, 0.5 mmol/EDTA) was used (Ct values of about 30). Each DNA isolation was repeated. 3 TaqMan reactions were set up for each eluate. From the 6 Ct values thus obtained, mean values were calculated (MW-Ct). The degree of inhibition was calculated as the difference from the MW-$Ct_{Eluate}$ minus MW-$Ct_{P2}$ (=$\Delta$Ct, delta Ct). Non-inhibitory eluates therefore have $\Delta$Ct values of 0 (in practice±1), whereas totally inhibitory DNA eluates have $\Delta$Ct values of 16 to 20.

Figure 1:
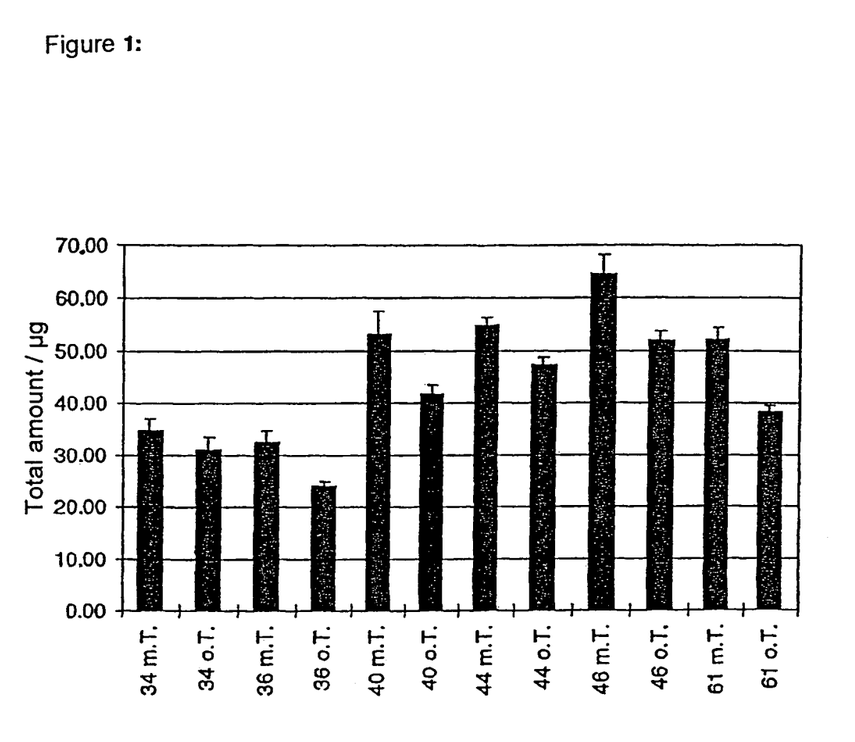
FIG. 1: Yields of DNA isolation according to process V2 and V3 of Example 2 from various stool samples. The values given are averages and the mean deviation from the total yields in μg. The first two numbers of the captions on the X axis are the code for the particular stool sample. The abbreviation m.T. (with tablet) denotes process V2 from Example 2, while o.T. (without tablet) denotes process V3.
Figure 2:
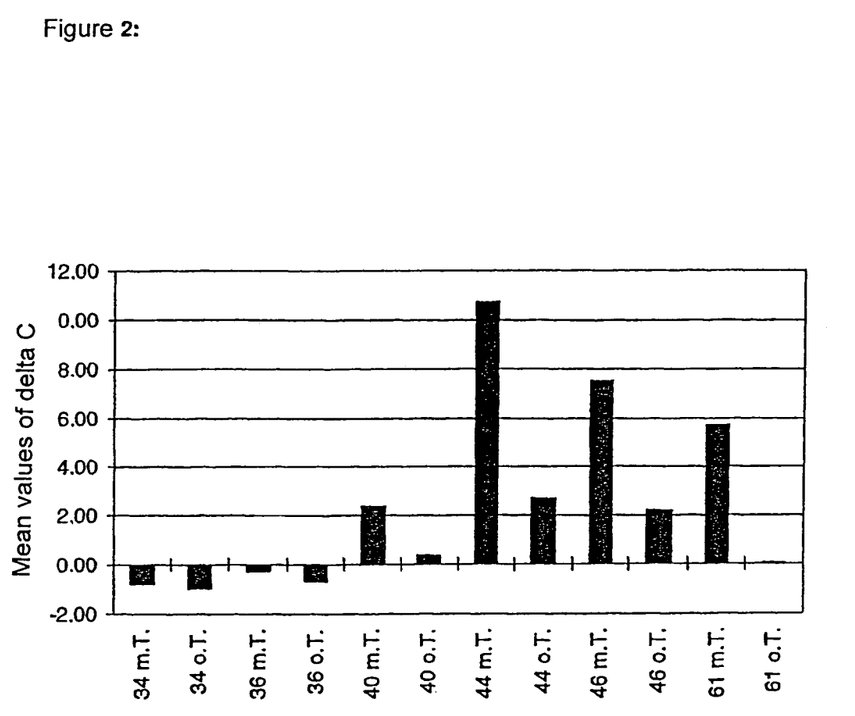
FIG. 2: Inhibiting PCR reaction by DNA preparations according to processes V2 and V3 from Example 2 from various stool samples. The first two numbers of the captions on the x axis indicate the code for the particular stool sample. The abbreviation m.T. indicates process V2 from Example 2, while o.T. indicates proves V3. For the calculation of the value delta Ct see Example 2. The PCR reaction was carried out in the presence of 10 ng of BSA/µl (BSA=bovine serum albumin).
Figure 3:
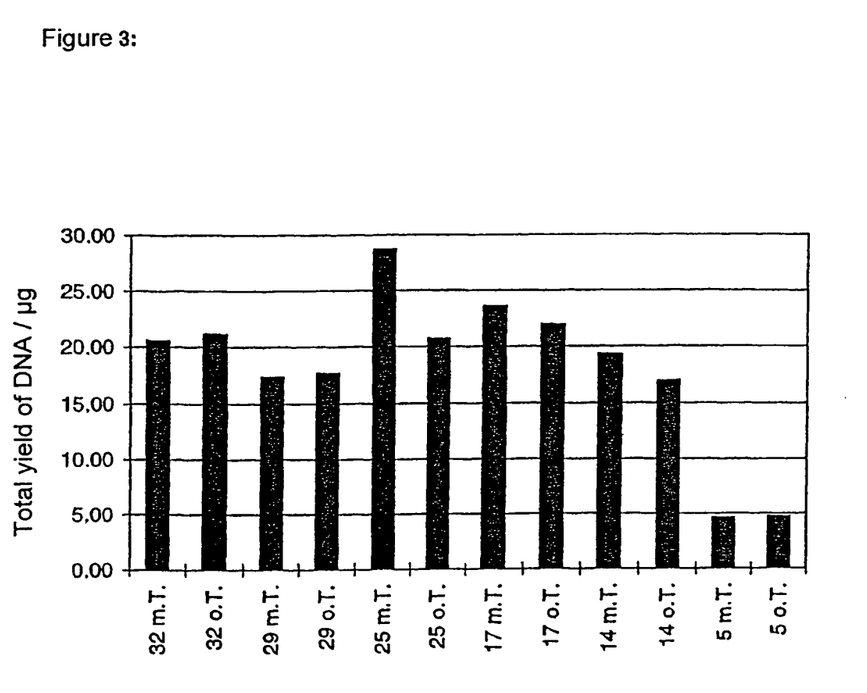
FIG. 3: Yields of DNA isolation according to processes V2 and V3 of Example 2 from various stool samples. The values are the averages of the total yields in µg. The first two numbers of the captions on the x axis indicate the code for the particular stool sample. The abbreviation m.T. indicates process V2 of Example 2 while o.T. indicates process V3.
Figure 4:
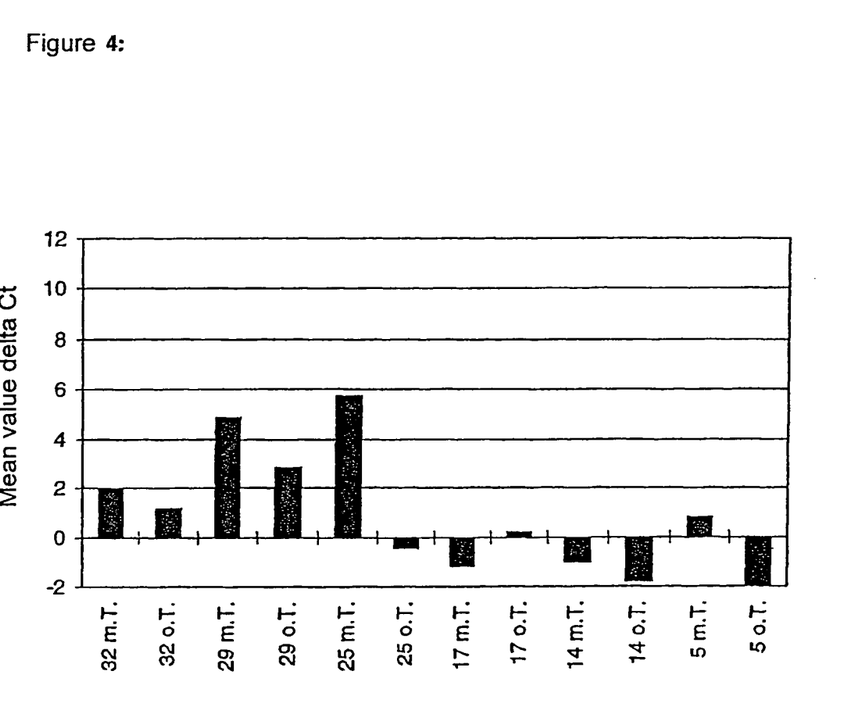
FIG. 4: Inhibiting PCR reaction by DNA preparations according to processes V1, V2 and V3 from Example 2 from various stool samples. The first two numbers of the captions on the x axis indicate the code for the particular stool sample. The abbreviation m.T. indicates process V2 from Example 2, while o.T. indicates proves V3. For the calculation of the value delta Ct see Example 2. The PCR reaction was carried out in the presence of 10 ng of BSA/µl (BSA=bovine serum albumin).
Figure 5:
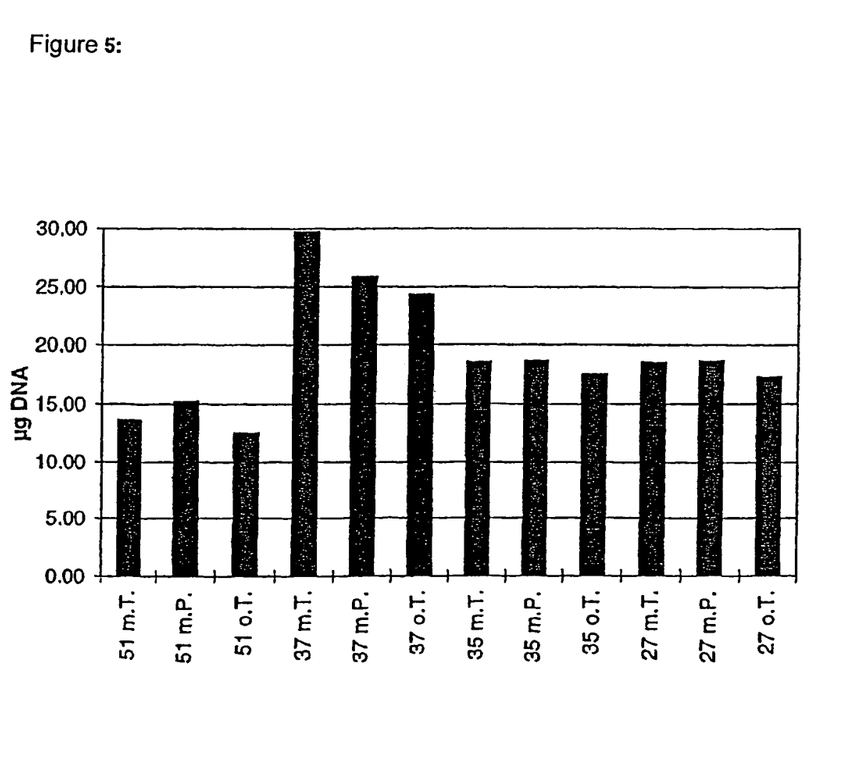
FIG. 5: Yields of DNA isolation according to processes V1, V2 and V3 of Example 2 from various stool samples. The values are the averages of the total yields in µg. The first two numbers of the captions on the x axis indicate the code for the particular stool sample. The abbreviation m.T. indicates process V2 of Example 2 while o.T. indicates process V3, and m.P. denotes the process V1.
Figure 6:
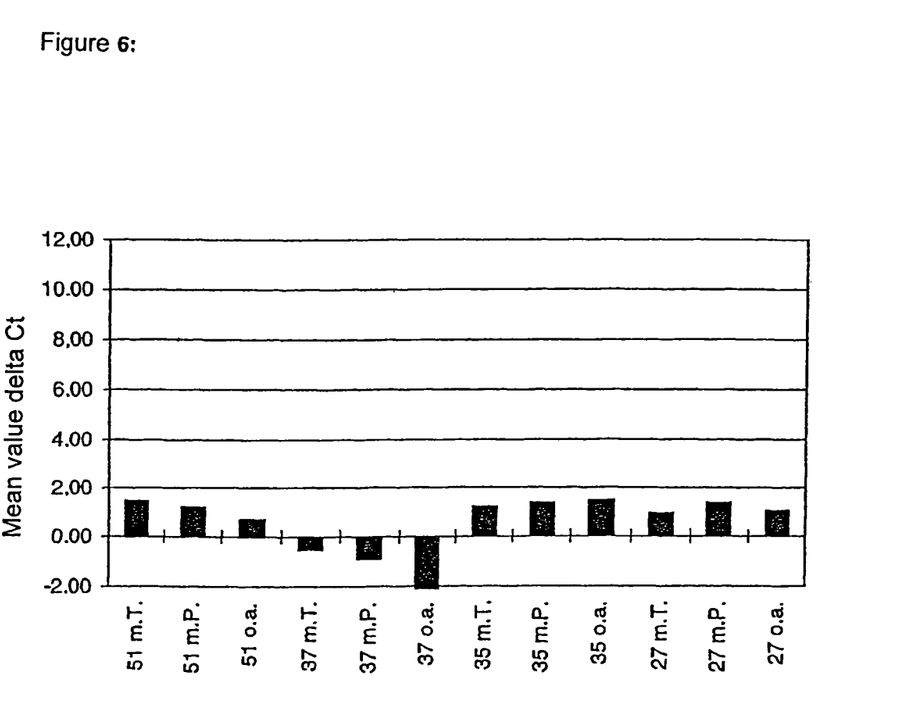
FIG. 6: Inhibiting PCR reaction by DNA preparations according to processes V1; V2 and V3 from Example 2 from various stool samples. The first two numbers of the captions on the x axis indicate the code for the particular stool sample. The abbreviation m.T. indicates process V2 from Example 2, while o.a. indicates proves V3, and m.P. denotes the process V1. For the calculation of the value delta Ct see Example 2. The PCR reaction was carried out in the presence of 10 ng of BSA/µl (BSA=bovine serum albumin).

Surprisingly, it was found that in order to remove inhibitory contaminants, there is no need to add an adsorption matrix when working up the sample (processes V1, V2) if the buffer according to the invention is used (process V3). The results of total yield and inhibitor content are shown in FIGS. 1 to 6.

Figure 7:
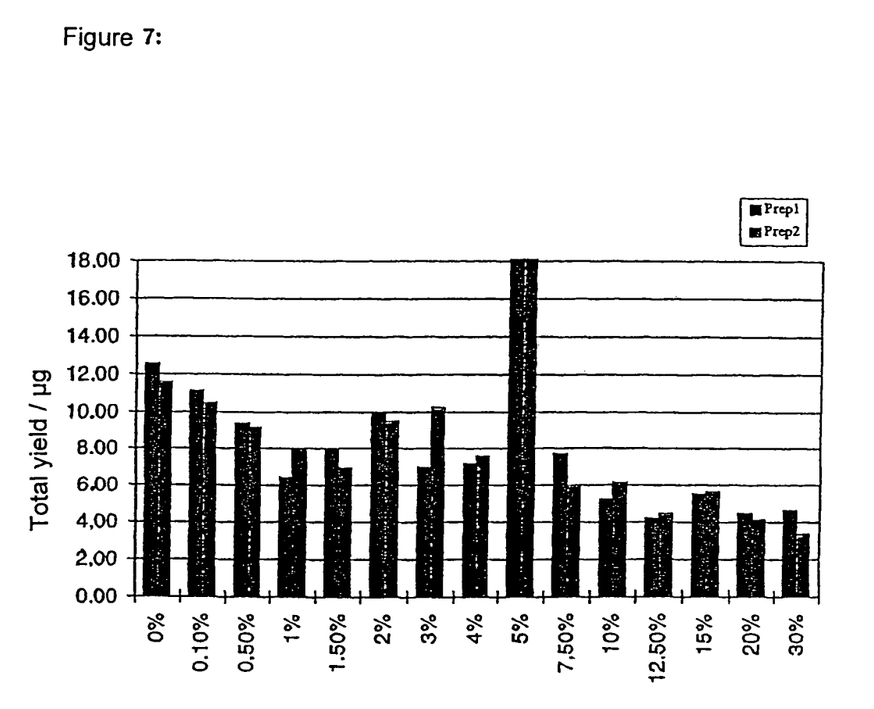
FIG. 7: Yields of DNA isolation according to the process in Example 3 as a function of the PVP concentration of the buffer P1. Value in µg of total yield. PVP concentration in % (wt/vol). Stool sample 27. Measurements repeated.
Figure 8:
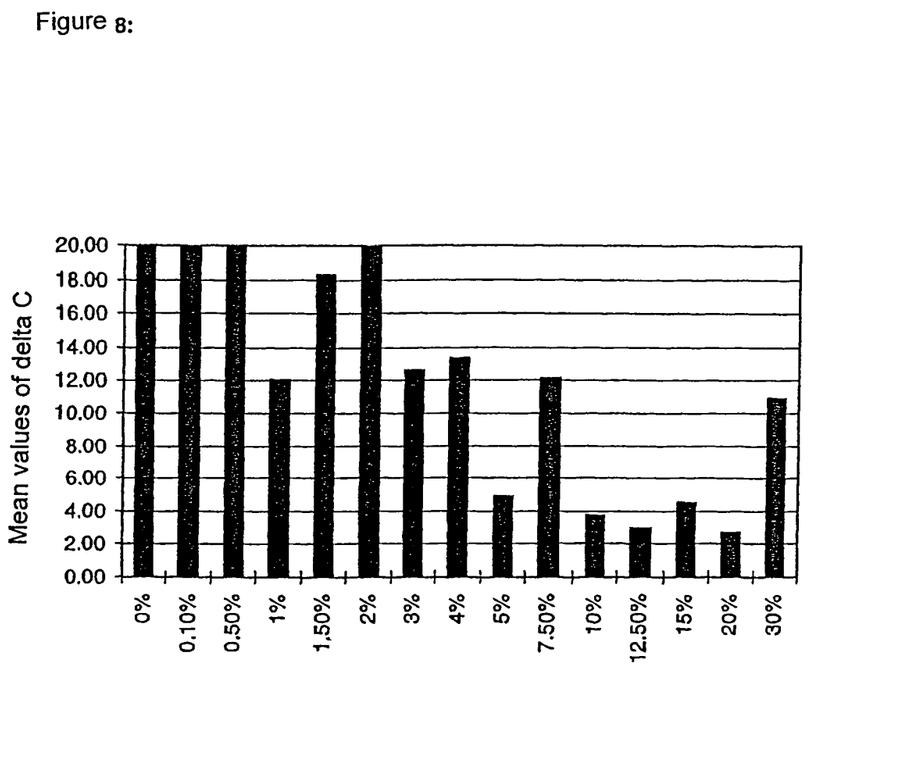
FIG. 8: Inhibition of PCR reaction by DNA preparations using the method of Example 3 as a function of the PVP concentration of the buffer P1. Stool sample 27. 1 ng/µl of BSA.
Figure 9:
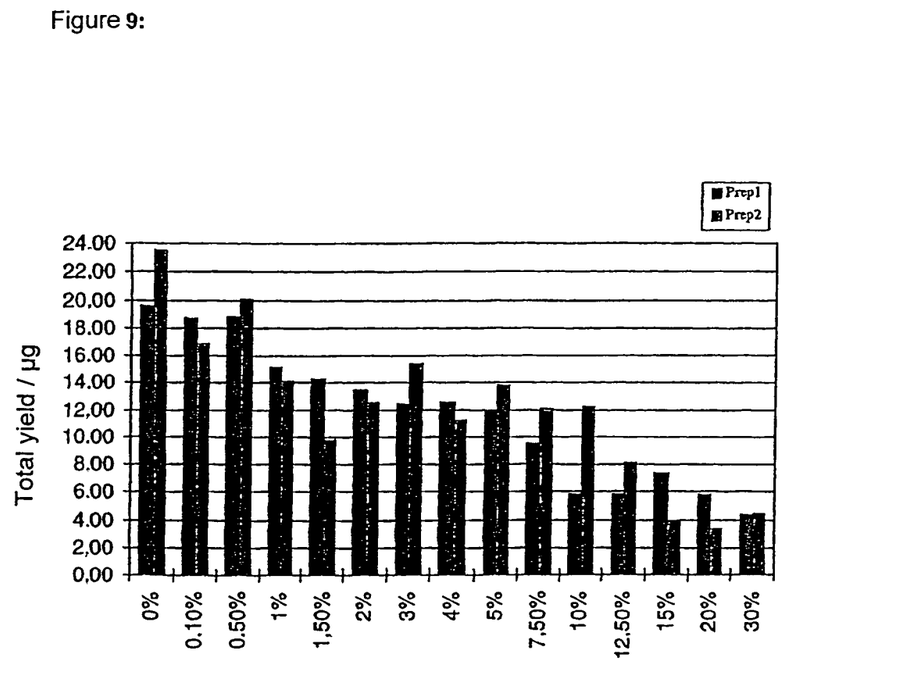
FIG. 9: Yields of DNA isolation according to the process in Example 3 as a function of the PVP concentration of the buffer P1. Value in µg of total yield. PVP concentration in % (wt/vol). Stool sample 61. Measurements repeated.
Figure 10:
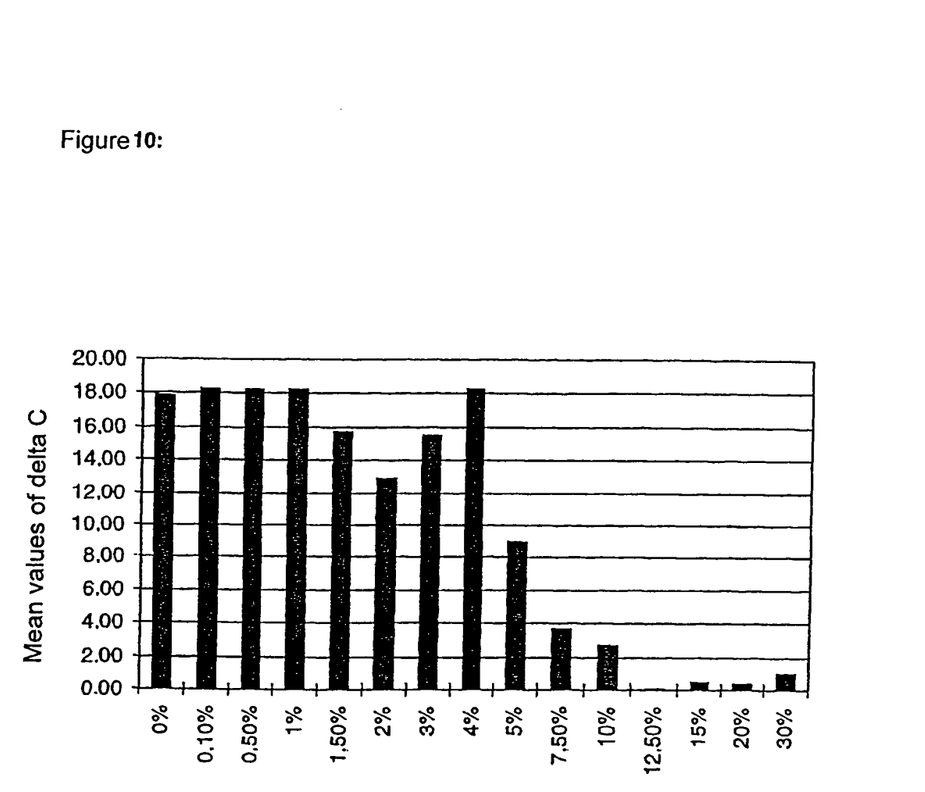
FIG. 10: Inhibiting the PCR reaction by DNA preparations according to the process of Example 3 as a function of the PVP concentration of the buffer P1. Stool sample 61. 1 ng/µl of BSA.
Figure 11:
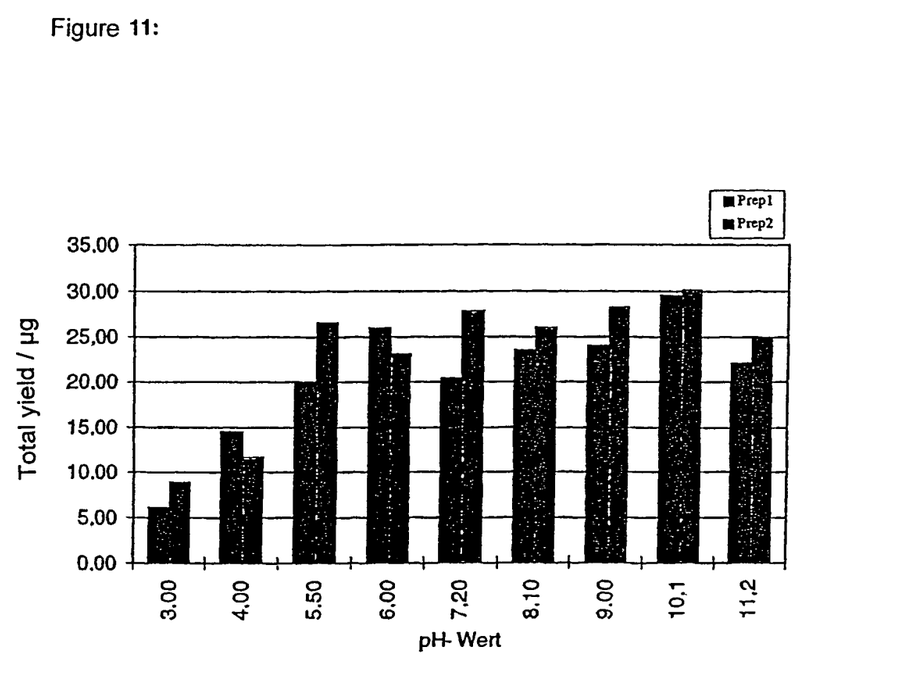
FIG. 11: Yields of DNA isolation according to the process of Example 3 as a function of the pH of the buffer P1. Value in µg of total yield. Stool sample 51. Measurements repeated twice.
Figure 12:
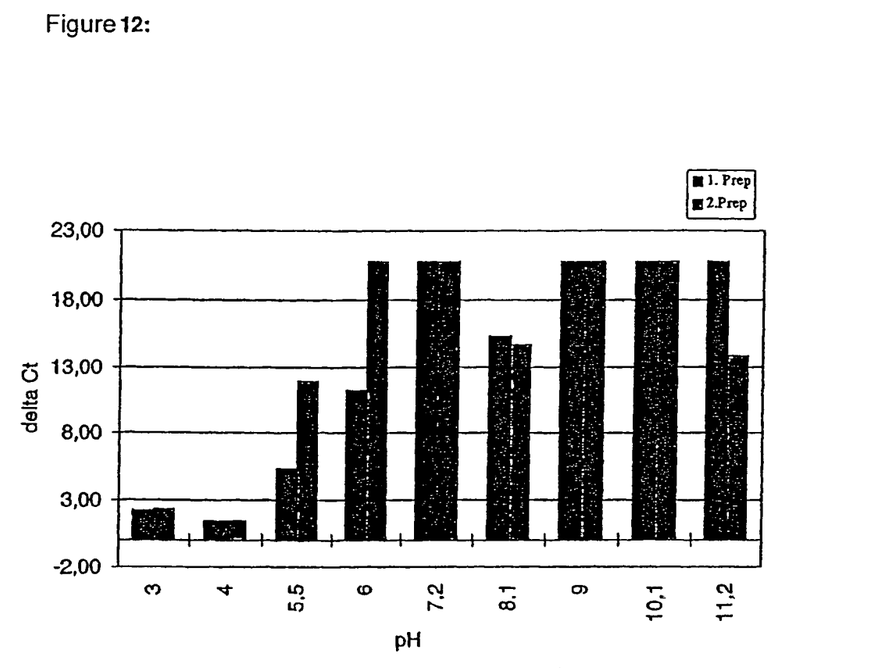
FIG. 12: Inhibiting PCR reaction by DNA preparations according to the process of Example 3 as a function of the pH of the buffer P1. Stool sample 51. 1 ng/µl BSA.

Example 3: Isolation of DNA from Stool Samples as a Function of Various Parameters of the Buffer DNA was isolated from stool samples according to the process of Example 1. In buffer P1 the concentration of polyvinylpyrrolidone was varied (from 0 to 30%) in a series of experiments and in a second series of experiments the pH of the buffer was varied (pH 3 to 11.2). The results for the total yield and inhibitor content are shown in FIGS. 7 to 12.

The invention claimed is:

1. A process for isolating or purifying nucleic acids from a sample of biological material contaminated with substances which inhibit enzymatic manipulation of the nucleic acids, comprising
   (1) contacting the sample with a buffer:
      (a) having a pH of 2 to 6.5,
      (b) having a salt concentration of at least 100 mmol/l, and
      (c) containing a phenol-neutralizing substance,
   to obtain a mixture of the sample and buffer; wherein no adsorption matrix based on carbohydrates is added to the sample, the mixture of sample and buffer, or any homogenisate, lysate or extract derived therefrom, and
   (2) purifying or isolating said nucleic acids from said mixture using an inorganic or organic carrier,
   thereby reducing the amount of the substances which inhibit enzymatic manipulation of the nucleic acids in said mixture,
   wherein said biological material is selected from the group consisting of: fecal material, animal tissue, tissue or cell cultures, bone marrow, human and animal body fluids, blood, serum, plasma, urine, sperm, cerebrospinal fluid, sputum and smears, fungi, plants, plant parts and extracts, prokaryotic or eukaryotic microorganisms, fossilized or mummified samples, soil samples, clarified sludge and sewage.

2. The process according to claim 1, wherein the buffer has a salt concentration of at least 250 mmol/l.

3. The process according to claim 1 or 2, wherein the salt contained in the buffer is selected from LiCl, NaCl, KCl, and combinations thereof.

4. The process according to claim 3, wherein the salt contained in the buffer is LiCl and is present in a concentration of 0.5 mol/l up to the limit of solubility.

5. The process according to claim 4, wherein the concentration of LiCl is 0.5 mol/l to 2.5 mol/l.

6. The process according to claim 1, wherein the buffer additionally contains at least 0.1% (wt/vol) of a detergent.

7. The process according to claim 1 or 6, wherein the buffer additionally contains at least 10 mmol/l of a chelating agent.

8. The process according to claim 1 or 6, wherein the buffer has a pH of more than 3 but less than 6.5.

9. The process according to claim 1 or 6, wherein the buffer contains at least 0.5% wt/vol of polyvinylpyrrolidone as the phenol-neutralizing substance.

10. The process according to claim 9, wherein the concentration of polyvinylpyrrolidone in the buffer is 1-30% (wt/vol).

11. The process according to claim 1, wherein the mixture of sample and buffer or a homogenisate or extract derived therefrom is incubated at a temperature of at least 50° C.

12. The process of claim 1, wherein the phenol-neutralizing substance is in the buffer at a concentration of 2-15% wt/vol.

13. The process of claim 1, wherein the phenol-neutralizing substance is in the buffer at a concentration of 4-10% wt/vol.

14. The process of claim 1, wherein said sample of biological material is a stool sample.

15. The process of claim 1, further comprising incubating the mixture under conditions sufficient for releasing or further releasing the nucleic acids from said biological material.

16. The process of claim 15, wherein said releasing or further releasing comprises chemical, thermal and/or enzymatic treatment of said mixture.

17. The process of claim 1, wherein said inorganic carrier is selected from porous metal oxides, non-porous metal oxides, silica gels, modified glass particles, unmodified glass particles, ground glass, quartz, zeolite, and combinations thereof, and wherein the organic carrier is selected from latex particles optionally modified with functional groups and synthetic polymers.

18. A process for isolating or purifying nucleic acids from a sample of biological material contaminated with substances which inhibit enzymatic manipulation of the nucleic acids comprising the following steps:
   (a) taking a sample of biological material containing nucleic acids, (b) contacting said sample with a buffer which has a pH of 2 to 6.5, has a salt concentration of at least 100 mmol/l, and polyvinylpyrrolidone (PVP), to obtain a mixture of the sample and buffer, wherein no adsorption matrix based on carbohydrates is added to the sample, the mixture of sample and buffer, or an extract, lysate or homogenisate derived therefrom, and, (c) purifying or isolating said nucleic acids from said mixture using an inorganic or organic carrier and releasing or further releasing said nucleic acids from said mixture of the sample and buffer thereby reducing the amount of inhibitory substances in said mixture of the sample and buffer and/or other contaminants in said mixture of the sample and buffer, wherein said biological materials are selected from the group consisting of: fecal material, animal tissue, tissue or cell cultures, bone marrow, human and animal body fluids, blood, serum, plasma, urine, sperm, cerebrospinal fluid, sputum and smears, fungi, plants, plant parts and extracts, prokaryotic or eukaryotic microorganisms, fossilized or mummified samples, soil samples, clarified sludge, and sewage.

19. The process according to claim 18 further comprising homogenizing the mixture of said sample and said buffer.

20. The process of claim 19, wherein the polyvinylpyrrolidone is in the buffer at a concentration of 2-15% wt/vol.

21. The process according to claim 18 further comprising homogenizing the biological materials prior to contacting said sample with the buffer which has a pH of 2 to 6.5, has a salt concentration of at least 100 mmol/l, and contains the PVP.

22. The process of claim 18 or 19, wherein the salt is selected from NaCl, KCl and LiCl, and is at a concentration of at least 399 mmol/l.

23. The process of claim 18 or 19, wherein the pH of the buffer is 4 to 6.5.

24. The process of claim 18 or 19, wherein the pH of the buffer is 5 to 6.

25. The process of claim 18 or 19, in which the buffer additionally contains 0.1% wt/vol of a detergent and/or at least 20 mmol/l of a chelating agent.

26. The process of claim 18 or 19, wherein the polyvinylpyrrolidone is in the buffer at a concentration of 4-10% wt/vol.

27. The process of claim 18 or 19, wherein the polyvinylpyrrolidone is in the buffer at a concentration of 1-30% wt/vol.

28. A process for isolating or purifying nucleic acids from a sample of biological material contaminated with substances which inhibit enzymatic manipulation of the nucleic acids comprising:

(a) taking a sample of biological material containing nucleic acids, (b) contacting said sample with a buffer which has a pH of 2 to 6.5, has a salt concentration of at least 100 mmol/l, and contains between 2-15% (wt/vol) of polyvinylpyrrolidone (PVP), wherein no adsorption matrix based on carbohydrates is added to the sample, the mixture of sample and buffer, or an extract, lysate or homogenisate derived therefrom, and, (c) purifying or isolating said nucleic acids from said mixture using an inorganic or organic carrier and releasing or further releasing said nucleic acids from said mixture of the sample and buffer thereby reducing the amount of inhibitory substances in said mixture of the sample and buffer and/or other contaminants in said mixture of the sample and buffer, and, wherein said biological materials are selected from the group consisting of: fecal material, animal tissue, tissue or cell cultures, bone marrow, human and animal body fluids, blood, serum, plasma, urine, sperm, cerebrospinal fluid, sputum and smears, fungi, plants, plant parts and extracts, prokaryotic or eukaryotic microorganisms, fossilized or mummified samples, soil samples, clarified sludge and sewage.

* * * * *